United States Patent [19]

Sullivan et al.

[11] 4,248,805
[45] Feb. 3, 1981

[54] VULCANIZABLE RUBBER COMPOSITIONS CONTAINING N-(SULFENYL) PHTHALAMIDES AS SCORCH INHIBITORS

[75] Inventors: Alfred B. Sullivan, Wadsworth; Raleigh W. Wise, Akron, both of Ohio

[73] Assignee: Monsanto Company, St. Louis, Mo.

[21] Appl. No.: 33,653

[22] Filed: Apr. 26, 1979

[51] Int. Cl.³ .................. C08F 8/34; C08C 19/00
[52] U.S. Cl. ................. 260/780; 260/453 R; 525/332; 525/351
[58] Field of Search ............. 260/780; 525/332, 330, 525/351

[56] References Cited

U.S. PATENT DOCUMENTS

| | | | |
|---|---|---|---|
| 3,546,185 | 12/1970 | Coran | 260/780 X |
| 3,732,271 | 5/1973 | Boustany | 260/780 X |
| 3,839,303 | 10/1974 | D'Amico | 260/780 X |
| 4,156,680 | 5/1979 | Morita | 260/45.85 A |

Primary Examiner—C. A. Henderson
Attorney, Agent, or Firm—Larry R. Swaney

[57] ABSTRACT

Vulcanizable rubber compositions are described which are inhibited from premature vulcanization by inhibitors consisting of a class of N, N'-disulfenyl phthalamides of the formula

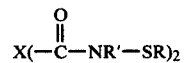

in which X is phenylene.

14 Claims, No Drawings

VULCANIZABLE RUBBER COMPOSITIONS CONTAINING N-(SULFENYL) PHTHALAMIDES AS SCORCH INHIBITORS

This invention relates to improved vulcanizable rubber compositions inhibited from premature vulcanization and to novel N,N'-disulfenyl phthalamides which are potent premature vulcanization inhibitors.

BACKGROUND OF THE INVENTION

The use of N-sulfenyl derivatives of amides to inhibit premature vulcanization of rubber is known. For example N-sulfenyl mono-amides and N-sulfenyl di-amides are described in U.S. Pat. Nos. 3,546,185 and 3,732,271, respectively. However, heretofore N,N'-disulfenyl derivatives of di-amides and their use as scorch inhibitors have not been described.

SUMMARY OF THE INVENTION

Accordingly, it has now been discovered that N,N'-disulfenyl derivatives of phthalamide, terephthalamide and isophthalamide are especially potent premature vulcanization inhibitors. Vulcanizable rubber compositions of the invention comprise sulfur-vulcanizable rubber, sulfur-vulcanizing agent, organic vulcanization accelerating agent and, in an amount effective to inhibit premature vulcanization, a compound of the formula

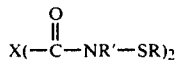

in which X is phenylene and R and R' are the same or different carbyl radicals selected from the group consisting of alkyl of 1–20 carbon atoms, cycloalkyl of 5–12 carbon atoms, phenyl or mono- or di-substituted phenyl wherein the substituents are lower alkyl, lower alkoxy or halo, or R' is hydrogen, when X is 1,2-phenylene R' is carbyl radical and when X is 1,3 phenylene or 1,4 phenylene R' is carbyl radical or hydrogen. Compounds in which R is cycloalkyl of 5–8 carbon atoms or secondary alkyl of 3–8 carbon atoms are preferred. Compounds in which X is 1,2 phenylene and R' is phenyl and in which X is 1,3 phenylene and R' is hydrogen comprise more preferred classes.

A preferred method for preparing inhibitors of the invention comprises reacting a sulfenyl chloride with an alkali metal (preferably sodium or potassium) salt of phthalamide, isophthalamide or terephthalamide. The alkali metal salt may be prepared by reacting the appropriate phthalamide and sodium or potassium methoxide in a polar solvent and distilling methanol from the reaction mixture.

Examples of satisfactory radicals for R are methyl, ethyl, propyl, isopropyl, n-butyl, sec.butyl, isobutyl, t-butyl, pentyl, sec.pentyl(1-methyl-1-butyl), hexyl, heptyl, octyl, t-octyl, nonyl, decyl, dodecyl, eicosyl, cyclopentyl, cyclohexyl, 2-methylcyclohexyl, 4-methylcyclohexyl, cycloheptyl, cyclooctyl, cyclodecyl, cyclododecyl, phenyl, 2-methylphenyl, 3-methylphenyl, 4-methylphenyl, 2-methyl-4-t-butylphenyl, 4-t-butylphenyl, 3-isopropylphenyl, 4-methoxyphenyl, 4-methylthiophenyl, 4-chlorophenyl and 2,4-dichlorophenyl. Hydrocarbon radicals are preferred. Preferred alkyl radicals are lower alkyl radicals of 1–5 carbon atoms.

Examples of novel compounds of the invention are:

N,N'-bis(Cyclohexylthio)isophthalamide
N,N'-bis(Cyclopentylthio)isophthalamide
N,N'-bis(Cyclooctylthio)isophthalamide
N,N'-bis(Phenylthio)isophthalamide
N,N'-bis(2-Methylphenylthio)isophthalamide
N,N'-bis(Methylthio)isophthalamide
N,N'-bis(Ethylthio)isophthalamide
N,N'-bis(n-Propylthio)isophthalamide
N,N'-bis(Isopropylthio)isophthalamide
N,N'-bis(n-Butylthio)isophthalamide
N,N'-bis(sec.Butylthio)isophthalamide
N,N'-bis(sec.Pentylthio)isophthalamide
N,N'-bis(Octylthio)isophthalamide
N,N'-bis(Decylthio)isophthalamide
N,N'-bis(Cyclohexylthio)phthalanilide
N,N'-bis(Cyclopentylthio)phthalanilide
N,N'-bis(Cyclooctylthio)phthalanilide
N,N'-bis(Phenylthio)phthalanilide
N,N'-bis(2-Methylphenylthio)phthalanilide
N,N'-bis(Methylthio)phthalanilide
N,N'-bis(Ethylthio)phthalanilide
N,N'-bis(n-Propylthio)phthalanilide
N,N'-bis(Isopropylthio)phthalanilide
N,N'-bis(n-Butylthio)phthalanilide
N,N'-bis(sec.Butylthio)phthalanilide
N,N'-bis(sec.Pentylthio)phthalanilide
N,N'-bis(Octylthio)phthalanilide
N,N'-bis(Decylthio)phthalanilide
N,N'-bis(Eicosylthio)phthalanilide
and the corresponding terephthalamides.

The inhibitors of the invention are incorporated into rubber stocks by mixing on a mill or in an internal mixer such as a Banbury mixer. However, the inhibitors may be incorporated by addition to latex, if desired. The process of the invention is particularly applicable to sulfur-vulcanizable rubber compositions which rubber compositions contain a sulfur vulcanizing agent such as an amine disulfide or a polymeric polysulfide but preferably, the vulcanizing agent is elemental sulfur. Rubber compositions containing organic accelerating agents are particularly improved by the inhibitors of the invention. Any organic accelerating agents in an amount effective (generally about 0.1–5 parts by weight accelerator per 100 parts by weight rubber) to accelerate the sulfur vulcanization of rubber is satisfactory in the practice of this invention. Examples of suitable accelerators are described in U.S. Pat. No. 3,546,185, col. 9, lines 53–75 and in U.S. Pat. No. 3,780,001, col. 4, lines 43–72. The inhibitors of the invention are effective with any sulfur-vulcanizable natural and synthetic rubber and mixtures thereof and especially effective with diene rubbers. Examples of satisfactory rubbers are described in U.S. Pat. No. 3,546,185, col. 10, lines 15–21 and U.S. Pat. No. 3,780,001, col. 5, lines 5–33. The vulcanizable composition may also contain conventional compounding ingredients such as reinforcing pigments, extenders, processing oils, antidegradants and the like.

Small amounts of inhibitors are effective to inhibit premature vulcanization. Improvements in processing safety may be observed with 0.05 parts or less of inhibitor per 100 parts rubber. Although there is no upper limit in the amount of inhibitor used, generally the amount does not exceed 5 parts inhibitor per 100 parts rubber. Typically, the amount of inhibitor added is about 0.1 to 2.5 parts per 100 parts rubber with amounts of about 0.2 to 1 part inhibitor per 100 parts rubber being commonly used. Methods for determining scorch times and curing characteristics of rubber stocks used in demonstrating this invention are described in U.S. Pat. No. 3,546,185, col. 13, lines 30-53. Stress-strain properties are reported in megapascals (MPa).

DESCRIPTION OF THE PREFERRED EMBODIMENTS

Compounds of the invention may be prepared by reacting sulfenyl chloride with the appropriate di-amide in the presence of a hydrogen chloride acceptor. Preferably, a sulfenyl chloride is reacted with an alkali metal salt of the di-amide. The alkali metal salt of the di-amide is prepared by reacting alkali metal alkoxide and di-amide followed by removal of the alcohol by-product by distillation. Another procedure comprises reacting a N,N'-(dihalo)-di-amide with a thiol, for example, N,N'-dibromo-isophthalamide is reacted with mercaptocycloalkane, thiophenol or mercaptoalkane.

EXAMPLE 1

To a suitable reactor equipped with temperature controlling means and stirring means, there are charged 41 g. (0.25 moles) terephthalamide, 108 g. of 25% sodium methoxide and 250 N-methylpyrrolidinone. Methanol is removed from the reactor by distillation until the temperature reaches about 125°-130° C. Benzene is added dropwise until the refluxing reactor temperature is about 78° C. While stirring the solution, cyclohexane sulfenyl chloride (0.5 mole) in 150 ml of benzene is added over a ½ hour period at 50°-70° C. The reaction is quenched with water and the solid product is recovered by filtration. The solid is recrystallized twice from methanol. N,N'bis-(cycloheyxlthio)terephthalamide, m.p. 230°-231° C., is obtained.

EXAMPLE 2

The procedure of Example 1 is followed except isophthalamide is charged in place of terephthalamide. N,N'bis-(Cyclohexylthio)isophthalamide, m.p. 182°-183° C. recrystallized from acetic acid, is obtained. Chemical analysis gives 6.87% N and 15.16% S compared with 6.52% N and 14.82% S calculated for $C_{20}H_{28}N_2O_2S_2$. The sulfur nitrogen ratio obtained is 2.21 versus 2.27 theory. NMR analysis indicates the desired product is obtained.

EXAMPLE 3

The procedure of Example 1 is followed except benzene sulfenyl chloride is used in place of cyclohexanesulfenyl chloride. N,N'bis(Phenylthio)terephthalamide is obtained. NMR analysis gives a spectra consistent with the indicated product. Chemical analysis gives 7.04% N and 15.97% S compared with 7.36% N and 16.85% S calculated for $C_{20}H_{16}N_2O_2S_2$. The sulfur-nitrogen ratio obtained is 2.27 versus 2.29 theory.

EXAMPLE 4

The procedure of Example 2 is followed except benzene sulfenyl chloride is charged. N,N'-bis(Phenylthio) isophthalamide, m.p. 171°-172° C. recrystallized from isopropanolbenzene mixture, is obtained. Chemical analysis gives 6.29% N and 14.59% S compared with 7.36% N and 16.85% S calculated for $C_{20}H_{16}N_2O_2S_2$. The sulfur-nitrogen ratio is 2.32 versus 2.29 theory. Identification of the product is confirmed with liquid chromographic analysis.

EXAMPLE 5

The disodium salt of phthalanilide is prepared by mixing dimethyl phthalate (52.4 g., 0.27 mole), aniline (50.2 g., 0.5 mole) and 25% sodium methoxide methanol solution (108 g., 0.5 mole) at room temperature. The mixture is heated with stirring to remove methanol. Distillation is continued until a refractive index of 1.4953 is obtained. A pale yellow solid is recovered by filtration, washed with hexane, and dried. 91.8 grams of disodium phthalanilide is recovered.

Cyclohexane sulfenyl chloride (made from cyclohexene mercaptan 34.8 g. and chlorine in toluene) is added slowly to a slurry of 54. g. disodium phthalanilide in 200 ml of toluene. The reaction mass is added to water and the salt by-product separated by filtration. The water and toluene layers are separated. The toluene layer is concentrated by evaporation and then treated with a 3/1 hexane/toluene mixture to precipate a solid product. N,N'-bis(Cyclohexylthio)phthalanilide, a buff colored solid, m.p. 172°-174° C., is recovered.

The invention is illustrated by using the following natural rubber and synthetic rubber stocks.

|  | Masterbatches | | |
| --- | --- | --- | --- |
|  | NR#1 | NR#2 | SBR |
| Smoked sheets | 100 | 100 | — |
| Oil-extended styrene-butadiene rubber 1712 | — | — | 89 |
| Cis-4-polybutadiene rubber | — | — | 35 |
| Carbon black | 45 | 40 | 67 |
| Zinc oxide | 3 | 5 | 3 |
| Stearic acid | 2 | 1 | 1 |
| Processing oil | 5 | 10 | 15 |
| Wax | — | 2 | 2 |
| N-(1,3-dimethylbutyl)-N'-(phenyl)-p-phenylenediamine | 2 | — | 2 |
|  | 157 | 158 | 214 |

TABLE 1

| Stocks | 1 | 2 | 3 | 4 | 5 | 6 | 7 | 8 |
| --- | --- | --- | --- | --- | --- | --- | --- | --- |
| NR masterbatch #1 | 157 | → | → | → | → | → | — | — |
| NR masterbatch #2 | — | — | — | — | — | — | 158 | 158 |
| Sulfur | 2.5 | → | → | → | → | → | → | → |
| N-tert-Butyl-2-benzothiazole-sulfenamide | 0.5 | → | → | → | → | → | 0.6 | 0.6 |
| N,N'-bis (Phenylthio)terephthalamide | — | 0.5 | — | — | — | — | — | — |
| N,N'-bis(Phenylthio)isophthalamide | — | — | 0.5 | — | — | — | — | — |
| N,N'-bis(Cyclohexylthio)terephthalamide | — | — | — | 0.5 | — | — | — | — |
| N,N'-bis(Cyclohexylthio)isophthalamide | — | — | — | — | 0.5 | — | — | — |
| N,N'-bis(Cyclohexylthio)phthalanilide | — | — | — | — | — | 0.5 | — | — |
|  | — | — | — | — | — | — | — | 0.4 |
| Mooney Scorch @ 121° C. | | | | | | | | |
| $t_5$, minutes | 28.5 | 36.5 | 52.5 | 33.5 | 93.5 | 104 | 42.3 | 89.0 |
| % increase in scorch delay | — | 28 | 84 | — | 179 | 210 | — | 110 |
| Stress-Strain @ 135° C. | | | | | | | | |
| $M_{300}$, MPa | 10.7 | 10.6 | — | 11.2 | 11.2 | 11.6 | 9.3 | 8.8 |
| UTS, MPa | 29.6 | 29.3 | — | 25.3 | 24.2 | 25.8 | 25.2 | 24.6 |

TABLE 1-continued

| Stocks | 1 | 2 | 3 | 4 | 5 | 6 | 7 | 8 |
| --- | --- | --- | --- | --- | --- | --- | --- | --- |
| Elong., % | 610 | 610 | — | 520 | 490 | 510 | 580 | 570 |

TABLE 2

| Stocks | 1 | 2 | 3 | 4 | 5 |
| --- | --- | --- | --- | --- | --- |
| SBR masterbatch | 214 | → | → | → | → |
| Sulfur | 2 | → | → | → | → |
| N-tert-Butyl-2-benzothiazole-sulfenamide | 1.2 | → | → | → | → |
| N,N'-bis(Phenylthio)terephthalamide | — | 0.5 | — | — | — |
| N,N'-bis(Phenylthio)isophthalamide | — | — | 0.5 | — | — |
| N,N'-bis(Cyclohexylthio)isophthalamide | — | — | — | 0.5 | — |
| N,N'-bis(Cyclohexylthio)phthalanilide | — | — | — | — | 0.5 |
| Mooney Scorch @ 135° C. | | | | | |
| $t_5$, minutes | 26.0 | 33.5 | 38.9 | 45.6 | 47.5 |
| % increase in scorch delay | — | 29 | 50 | 75 | 83 |
| Stress-Strain @ 135° C. | | | | | |
| $M_{300}$, MPa | 7.6 | 7.4 | 7.2 | 6.1 | 7.3 |
| UTS, MPa | 17.3 | 17.2 | 16.7 | 16.5 | 17.9 |
| Elong., % | 550 | 550 | 550 | 600 | 580 |

Portions of the masterbatches containing acclerator and sulfur but no inhibitor are controls. A quantity of inhibitor is incorporated into other portions of the masterbatches. The properties of the vulcanizable compositions are measured by conventional methods as described above. The results are shown in Tables 1 and 2.

The data show that the N,N'-bis(sulfenyl) compounds of the invention effectively inhibit premature vulcanization. The data further indicate that cyclohexylthio compounds exhibit greater potency than the corresponding phenylthio compounds and that the isophthalamide and phthalanilide compound exhibit greater potency than the corresponding terephthalamide compounds.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A vulcanizable rubber composition comprising sulfur-vulcanizable diene rubber, sulfur-vulcanizing agent, organic vulcanization accelerating agent and, in an amount effective to inhibit premature vulcanization, a compound of the formula

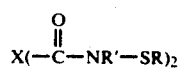

in which X is phenylene and R and R' are the same or different carbyl radicals selected from the group consisting of alkyl of 1–20 carbon atoms, cycloalkyl of 5–12 carbon atoms, phenyl or mono- or di-substituted phenyl wherein the substituents are lower alkyl, lower alkoxy or halo, or R' is hydrogen, when X is 1,2-phenylene R' is carbyl radical and when X is 1,3 phenylene or 1,4 phenylene R' is carbyl radical or hydrogen.

2. The composition of claim 1 in which the vulcanizing agent is elemental sulfur.

3. The composition of claim 2 in which X is 1,2-phenylene.

4. The composition of claim 2 in which X is 1,3-phenylene.

5. The composition of claim 2 in which X is 1,4-phenylene.

6. The composition of claim 3 in which R' is phenyl.

7. The composition of claim 6 in which R is cyclohexyl.

8. The composition of claim 4 in which R is cyclohexyl.

9. The composition of claim 8 in which R' is hydrogen.

10. The composition of claim 4 in which R is phenyl and R' is hydrogen.

11. The composition of claim 3 in which R is a secondary alkyl of 3–8 carbon atoms.

12. The composition of claim 4 in which R is secondary alkyl of 3–8 carbon atoms.

13. The composition of claim 11 in which R is isopropyl and R' is phenyl.

14. The composition of claim 12 in which R is isopropyl and R' is hydrogen.

* * * * *